US010478307B2

United States Patent
Wasielewski et al.

(10) Patent No.: US 10,478,307 B2
(45) Date of Patent: Nov. 19, 2019

(54) KNEE PROSTHESIS INCLUDING ROTATABLE POST

(71) Applicant: WM INNOVATIONS, LLC, Stanford, CA (US)

(72) Inventors: Ray C. Wasielewski, New Albany, OH (US); Stephen Edward White, Fort Wayne, IN (US)

(73) Assignee: WM INNOVATIONS, LLC, Stanford, CA (US)

( * ) Notice: Subject to any disclaimer, the term of this patent is extended or adjusted under 35 U.S.C. 154(b) by 56 days.

(21) Appl. No.: 15/892,011

(22) Filed: Feb. 8, 2018

(65) Prior Publication Data

US 2019/0240032 A1    Aug. 8, 2019

(51) Int. Cl.
*A61F 2/38* (2006.01)
*A61F 2/30* (2006.01)

(52) U.S. Cl.
CPC ............ *A61F 2/389* (2013.01); *A61F 2/3859* (2013.01); *A61F 2/3886* (2013.01); *A61F 2002/30621* (2013.01)

(58) Field of Classification Search
CPC .......... A61F 2/3868; A61F 2/389; A61F 2/38; A61F 2/34; A61F 2/32
See application file for complete search history.

(56) References Cited

U.S. PATENT DOCUMENTS

| | | | |
|---|---|---|---|
| 6,013,103 A | 1/2000 | Kaufman et al. | |
| 6,986,791 B1 * | 1/2006 | Metzger | A61F 2/3868 623/20.24 |
| 8,211,181 B2 | 7/2012 | Walker | |
| 8,292,964 B2 | 10/2012 | Walker | |
| 9,216,088 B2 * | 12/2015 | Wasielewski | A61F 2/3836 |
| 9,668,870 B2 * | 6/2017 | Wasielewski | A61F 2/3836 |
| 10,080,663 B2 * | 9/2018 | Wasielewski | A61F 2/3836 |
| 2014/0277534 A1 * | 9/2014 | Wasielewski | A61F 2/3836 623/20.27 |
| 2017/0020674 A1 | 1/2017 | Walker | |
| 2017/0079801 A1 | 3/2017 | Drury et al. | |

* cited by examiner

*Primary Examiner* — Jason-Dennis N Stewart
(74) *Attorney, Agent, or Firm* — Schwegman Lundberg & Woessner, P.A.

(57) ABSTRACT

A knee joint prosthesis for a tibia and femur can include a tibial component, a tibial bearing, and a post. The tibial bearing can include a first bearing portion, a second bearing portion, and an aperture. The first bearing portion can be positionable on a first side of the sagittal axis and can have a first shape. The second bearing portion can be positionable on a second side can have a second shape different than the first shape. The post, together with the first bearing portion and the second bearing portion, can be configured to promote the femur to pivot substantially about the first bearing portion.

20 Claims, 10 Drawing Sheets

KNEE PROSTHESIS INCLUDING ROTATABLE POST

FIELD

The present subject matter relates to orthopedic prostheses and, more particularly, to knee joint prostheses.

BACKGROUND

Orthopedic procedures and prostheses (or prosthetic implants) are commonly utilized to repair and/or replace damaged bone and tissue in the human body. For example, a knee arthroplasty can be performed to restore natural knee function by replacing damaged or diseased articular surfaces of the femur and/or tibia with artificial components. In many procedures, an incision is made into the knee joint to expose the bones comprising the joint. Cut guides can be used to guide the removal of one or more articular surfaces that are to be replaced so that prostheses can be installed to replicate the articular surfaces. Knee prostheses can include a femoral component implanted on a distal end of the femur. A tibial component can be implanted on a proximal end of a tibia and can receive a tibial bearing engageable with the femoral component. The femoral component can articulate with the tibial bearing component to replicate the function of a healthy natural knee. Various types of arthroplasties can be performed including a total knee arthroplasty, where all of the articulating compartments of the joint are repaired with prosthetic components.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

Orthopedic prostheses are commonly used to repair or replace damaged bone and tissue in a human body. A knee prosthesis, for example, can include a tibial component and a femoral component that can replace damaged or destroyed bone and tissue in the tibia and femur, respectively.

In certain total knee replacement (TKR) prostheses, such as "posterior stabilized" prostheses, a cam can be positioned in an intercondylar fossa of a femoral component to cooperate with a spine formed in a tibial component to promote or constrain motion within predefined boundaries. Some posterior stabilized prostheses can include a spine formed with a tibial bearing insert (sometimes referred to as a meniscal component) that interacts with a cam formed in a femoral component to promote femoral roll back during flexion of the TKR prosthesis. Posterior stabilized prostheses can be appropriate where a posterior cruciate ligament (PCL) is torn or otherwise damaged, or where the PCL is resected during surgery. In addition, some knee prostheses feature a hyperextension stop, which can be a posterior-facing structure formed in a femoral component configured to engage an anterior-facing surface of the tibial spine when the knee prosthesis is in a "full extension" or "hyperextension" orientation. Such a hyperextension stop can also be referred to as an anterior cam. In these knee prostheses, interaction between the femoral component and spine operates as a physical stop against extension of the knee prosthesis past a predetermined level of extension. Such knee prostheses can provide articulation similar to an anatomical articulation of a natural knee joint.

A natural knee experiences internal and external rotation, that is, rotation about a generally proximal-distal axis, during flexion. Internal/external rotation can be significant in deep flexion where an asymmetric anteroposterior roll-back can occur, i.e., the lateral femoral condyle rolls back faster and/or further than the medial condyle. Internal/external rotation is also significant as the natural knee experiences extension (e.g., 0-20 degrees), a phenomenon sometimes referred to as the "screw-home" mechanism. Knee prosthesis designs can seek to accommodate, promote or drive internal/external rotation to mimic operation of a natural knee; however, many designs offer only a simple hinge between the tibia and femur, which can cause undesired prosthesis wear and may cause patient discomfort.

This disclosure addresses the issues discussed above by providing a rotatable spine engageable with an intercondylar fossa and femoral cam to promote natural rotation and by providing an asymmetrically shaped tibial bearing to promote a medial pivot bias of the femoral prosthesis (and therefore femur) relative to the tibial prosthesis (and therefore tibia and fibula) enabling femoral rollback to promote natural knee movement during flexion and extension. That is, the bearing can be shaped to promote asymmetric anteroposterior rollback of a lateral femoral condyle of the femur at a faster rate than rollback of a medial femoral condyle. This can help to provide a more natural movement of a leg including these prostheses, helping to improve a patient's mobility. Also, by providing a prosthesis having a relatively more natural operational design, wear of the components of the prosthesis may be reduced helping reduce to reduce complications and revisions.

As used herein, the terms "proximal" and "distal" should be given their generally understood anatomical interpretation. The term "proximal" refers to a direction generally toward the torso of a patient, and "distal" refers to the opposite direction of proximal, i.e., away from the torso of a patient. It should be understood that the use of the terms "proximal" and "distal" should be interpreted as though the patient were standing with the knee joint in extension despite the apparatuses described herein generally being used with the knee joint in flexion. The intent is to differentiate the terms "proximal" and "distal" from the terms "anterior" and "posterior". As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior".

Figure 1A:
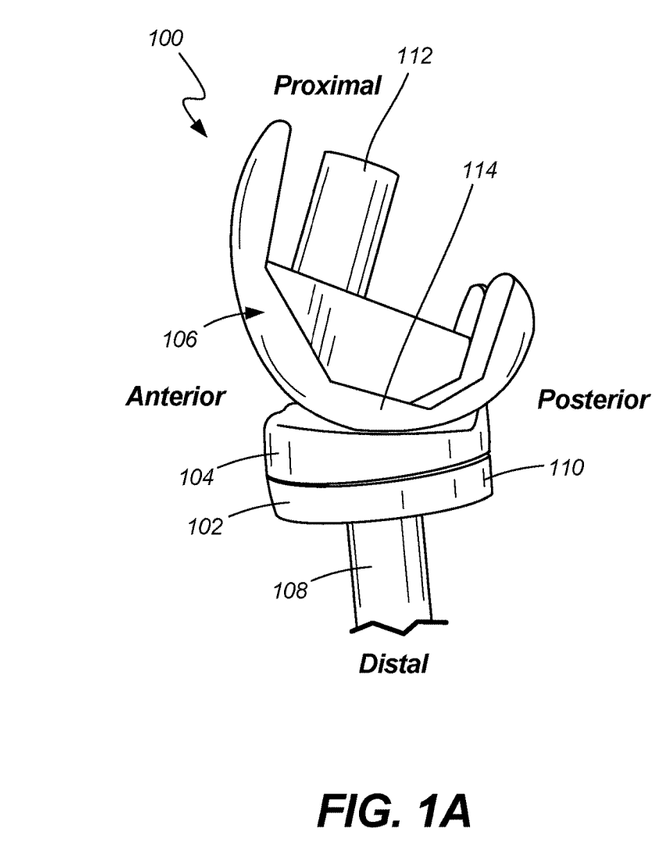
FIG. 1A illustrates an elevation view of an implant assembly from a lateral perspective, in accordance with at least one example of the present disclosure.

FIG. 1A illustrates an elevation view of implant assembly 100 from a lateral perspective, in accordance with at least one example of the present disclosure. Implant assembly 100 can include tibial component 102, tibial bearing 104, and femoral component 106. Tibial component 102 can include tibial stem 108 and tibial baseplate 110. Femoral component 106 can include femoral stem 112, and condyles 114 (one visible in FIG. 1A). Also shown in FIG. 1A are orientation indicators Proximal, Distal, Anterior, and Posterior.

As part of a knee arthroplasty, implant assembly 100 can be configured to be installed in place of a knee on a patient (not shown), in some examples, as a posterior-stabilized TKA prosthesis. In some examples, femoral component 106 can connect to a distal portion of a femur (not shown) and tibial component 102 can connect to a proximal portion of a tibia (not shown), as discussed further below.

Tibial component 102 can be a rigid member comprised of biocompatible materials, such as stainless steel alloys, titanium, cobalt-chromium, nickel-chromium, plastics, combinations thereof, and the like. Tibial component 102 can include tibial baseplate 110, which can include a relatively planar portion on a proximal portion of tibial component 102. Stem 108 can be a relatively cylindrical or prismatic member extending distally from a distal side of tibial baseplate 110. Stem 108 can be sized for insertion into a prepared tibial intramedullary canal and a distal portion of baseplate 110 can be sized and shaped to interface with a proximal portion of a resected tibia.

Tibial bearing 104 can be a rigid or semi-rigid member comprised of biocompatible and relatively low friction materials, such as plastics, metals composites, and the like. In some examples, tibial bearing 104 can be comprised of a polyethylene such as polyether ether ketone (PEEK). Tibial bearing 104 can be sized and shaped to engage and secure to a proximal side of tibial baseplate 110 at a distal portion of tibial bearing 104, such that tibial baseplate 110 can retain tibial bearing 104 thereon. A proximal portion of tibial bearing 104 can include an articular surface, configured to engage condyles of femoral component 106. Though not clearly shown in FIG. 1A, tibial bearing 104 can be asymmetrically shaped to promote a pivot of femoral component 106 about a medial side of tibial bearing 104, as discussed further below.

Femoral component 106 can be a rigid member comprised of biocompatible materials, such as stainless steel alloys, titanium, cobalt-chromium, nickel-chromium, plastics, combinations thereof, and the like. Femoral stem 112 can be a relatively cylindrical or prismatic member extending proximally from a proximal side of femoral component 106 and can be sized for insertion into a prepared femoral intramedullary canal. Condyles 114 can be radiused components located at a distal portion of femoral components 106 that can be shaped and sized to engage with and articulate with proximal surfaces of tibial bearing 104. An intercondylar fossa can be located between condyles 114. An overview of operation of the components of implant assembly 100 is discussed below with respect to FIGS. 1B and 1s discussed in further detail in the FIGS. that follow.

Figure 1B:
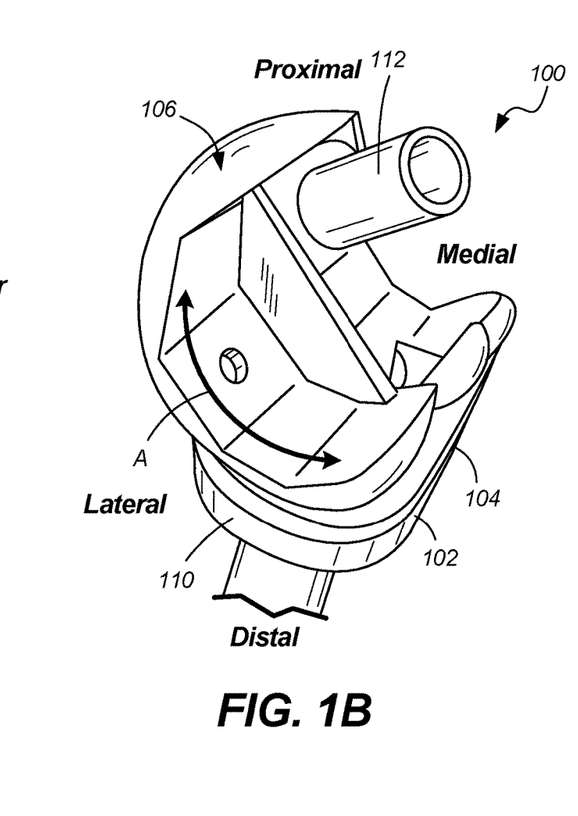
FIG. 1B illustrates an isometric view of an implant assembly from a proximal-lateral perspective, in accordance with at least one example of the present disclosure.

Implant 100 of FIG. 1B can be consistent with FIG. 1A discussed above; however, FIG. 1B shows how components of implant assembly 100 can move during operation following implantation, in one example. FIG. 1B illustrates an isometric view of implant assembly 100 from a proximal-lateral perspective, in accordance with at least one example of the present disclosure. Implant assembly 100 can include tibial component 102, tibial bearing 104, and femoral component 106. Tibial component 102 can include tibial stem 108 and tibial baseplate 110. Femoral component 106 can include femoral stem 112, and condyles 114 (one visible in FIG. 1B). Also shown in FIG. 1B are arc A, orientation indicators Proximal, Distal, Medial, and Lateral.

In operation of some examples, when femoral component 106 is installed in a femur of a patient and tibial component 102 is installed in a tibia of the patient. Tibial bearing 104 can be secured to tibial tray 110 of tibial component 102 such that condyles 114 interface with bearing surfaces of tibial bearing 104, such that the patient may operate their leg in normal flexion and extension. During these movements, the articulation of condyles 114 on tibial bearing 104 can cause femoral component 106 to pivot about medial insert congruity, or to pivot on a medial portion of tibial bearing 104, allowing the lateral femoral condyle 114 to move along arc A (shown in FIG. 1B) to promote natural rollback of the femur relative to the tibia, providing a more natural movement of the patient's leg, helping to improve the patient's mobility. Also, by providing implant assembly 100 having a relatively more natural operational design, wear of tibial component 102, tibial bearing 104, and femoral component 106 may be reduced, helping reduce to reduce complications and revisions.

Figure 2A:
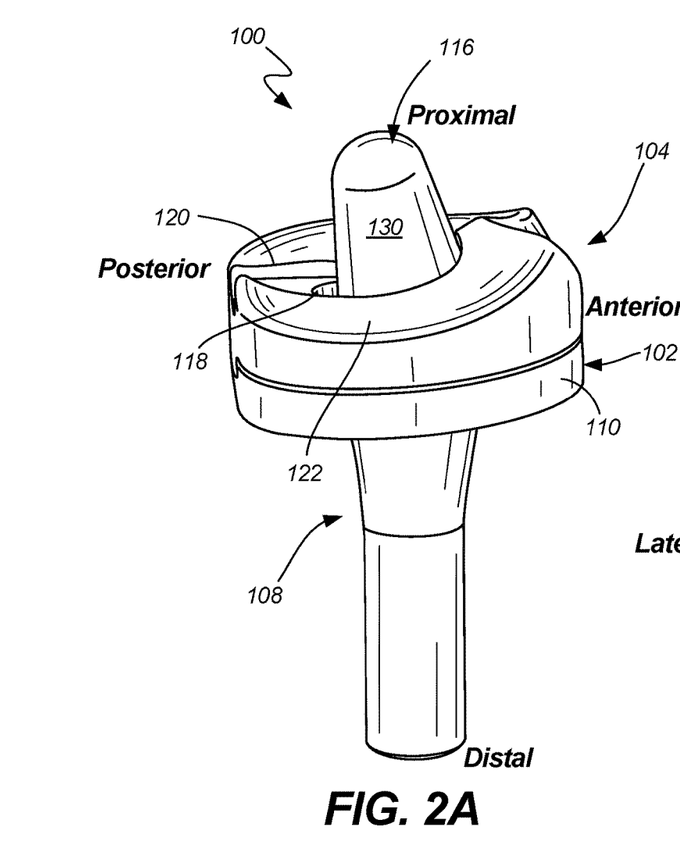
FIG. 2A illustrates an isometric elevation view of an implant assembly from a medial perspective, in accordance with at least one example of the present disclosure.
Figure 2B:
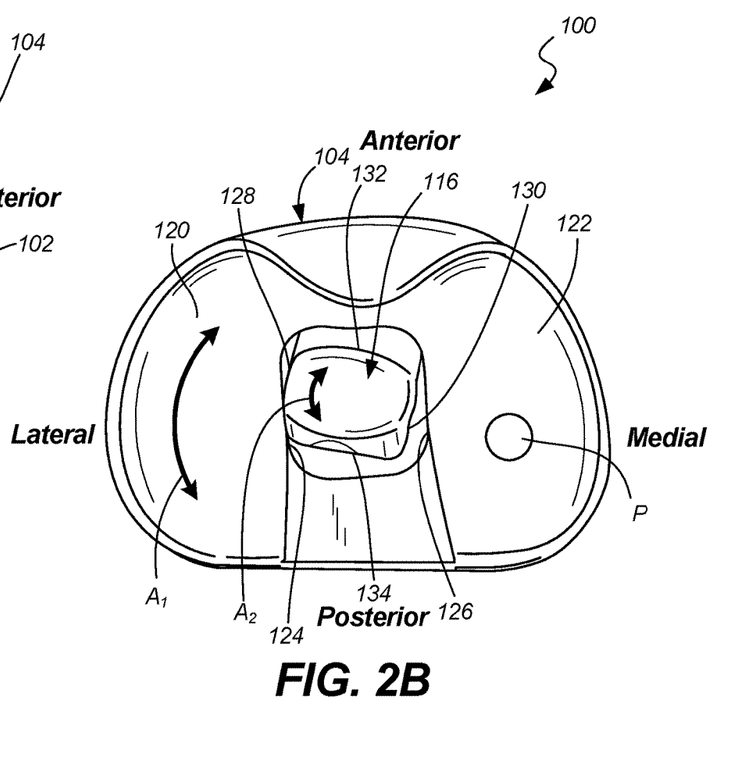
FIG. 2B illustrates an isometric view of an implant assembly from a proximal perspective, in accordance with at least one example of the present disclosure.

FIG. 2A illustrates an isometric elevation view of implant assembly 100 from a medial perspective, in accordance with at least one example of the present disclosure. FIG. 2B illustrates an isometric view of implant assembly 100 from a proximal perspective, in accordance with at least one example of the present disclosure. FIGS. 2A and 2B are discussed below concurrently.

Implant assembly 100 can include tibial component 102, tibial bearing 104, and post 116. Tibial component 102 can include tibial stem 108 and tibial baseplate 110. Tibial bearing 104 can include aperture 118, lateral bearing portion 120, and medial bearing portion 122. Aperture 118 can include lateral wall 124 and medial wall 126. Post 116 can include lateral face 128, medial face 130, anterior face 132, and posterior face 134. Also shown in FIG. 2A are orientation indicators Proximal, Distal, Anterior, and Posterior. Also shown in FIG. 2B are arc A1, arc A2, pivot P, and orientation indicators Anterior, Posterior, Medial, and Lateral.

Implant assembly 100 of FIGS. 2A and 2B can be consistent with implant assembly 100 shown in FIGS. 1A and 1B; FIGS. 2A and 2B show additional details of implant assembly 100. For example, FIGS. 2A and 2B show aperture 118 of tibial bearing 104, which can be a bore or hole through tibial bearing 104 and can be sized to receive post 116 therein and/or therethrough. Lateral wall 124 and medial wall 126 of aperture 118 can be walls of tibial bearing 104 partially forming aperture 118. FIGS. 2A and 2B also shows lateral portion 120 and medial portion 122 of tibial bearing 104. As shown in more detail in FIGS. 3A and 3B below, lateral portion 120 and medial portion 122 can be asymmetrically shaped and, in some examples, can include have different surface geometries, such as different radii of curvature into and along the transverse plane of tibial bearing 104. Also, lateral portion 120 and medial portion 122 can have different thicknesses.

Further, FIGS. 2A and 2B show post 116, which can be an elongate rigid member comprised of biocompatible materials, such as stainless steel alloys, titanium, cobalt-chromium, nickel-chromium, plastics, combinations thereof, and the like. Post 116 can include a tapered proximal portion partially defined by lateral face 128, medial face 130, anterior face 132, and posterior face 134. Post 116 can also include a distal portion (not shown in FIGS. 2A and 2B), where the distal portion is disposable through aperture 118 and into femoral stem 108 such that post 116 can rotate within femoral stem 108 and aperture 118.

In some examples, each of lateral face 128, medial face 130, anterior face 132, and posterior face 134 can be flat or can be rounded in multiple planes for ease of insertion through bearing 104 and for articulation with a cam of a femoral component, as discussed further below.

In operation of a natural knee, during flexion (such as in deep flexion), rollback of the femoral condyles can occur, where the lateral femoral condyle rolls back (posteriorly) faster and/or further than the medial condyle, such as by −1 to −25 degrees. The components of implant assembly 100 can promote this motion where post 116 can engage intercondylar fossa and a cam of a femoral component (such as femoral component 106 of FIGS. 1A and 1B) and the femoral condyles can engage lateral portion 120 and medial portion 122 of tibial bearing 104. Because post 116 is rotatable and because lateral portion 120 and medial portion 122 are asymmetrically shaped (differences in articular surface geometry and/or compartment thicknesses), post 116 and lateral portion 120 and medial portion 122 of tibial bearing 104 can promote asymmetric condyle roll, allowing the lateral condyle to roll back (or posteriorly) along arc A1 while post 116 rotates about arc A2 while the medial condyle substantially pivots about P.

Similarly, rotation is also significant as the natural knee approaches extension. During extension (such as in full or hyperextension), rollback (or forward roll) of the lateral femoral condyle can occur, where the lateral femoral condyle rolls anteriorly faster and/or further than the medial condyle such as by 1 to 25 degrees. As shown in FIG. 2B, post 116 can rotate along arc A2 to allow the lateral femoral condyle to rotate along arc A1 while the medial femoral condyle substantially pivots about P (though some translation of the medial femoral condyle may occur). Implant assembly 100 can therefore enable movement of a patient's leg that is more similar to natural movement than is provided by some implant assemblies of the prior art. By promoting more natural operation of the knee including implant assembly 100, patient mobility may be increased, pain may be reduced, and likelihood of injury may be reduced. Further, complications and revision may be reduced.

In some examples, rotation of post 116 can be limited by contact between lateral face 128 and lateral wall 124 of tibial bearing 104 and by medial face 130 making contact with medial wall 126 of tibial bearing 104. In some examples, rotation of post can be limited by contact of anterior face 132 and/or posterior face 134 with lateral wall 124 and/or medial wall 126. Similarly, edges of post 116 defined at the junction of each of lateral face 128, medial face 130, anterior face 132, and posterior face 134 can limit rotation of post 116 through contact with lateral wall 124 and/or medial wall 126. In some examples, lateral face 128 and medial face 130 can be substantially flat to help limit rotation. In other examples, each of lateral face 128 and medial face can be curved to limit rotation, as desired. In some examples, such contact can limit rotation to ±10 degrees from a neutral position. However, the size and shape of post 116 and aperture 118 can be configured to limit rotation to other angles, such as 1, 2, 3, 4, 5, 6, 7, 8, 9, 11, 12, 14, 16, 18, 20 degrees, and the like.

Figure 3A:
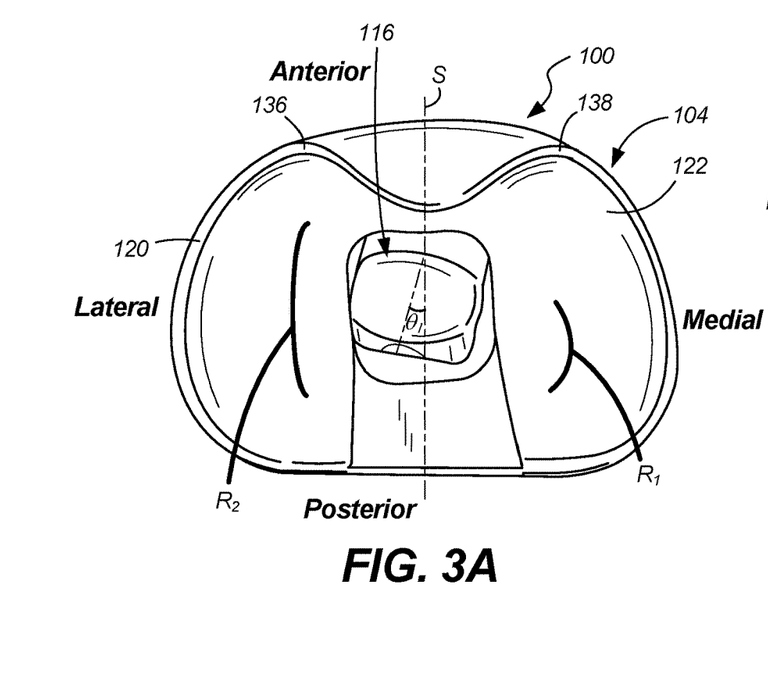
FIG. 3A illustrates a plan view of an implant assembly in a first condition, in accordance with at least one example of the present disclosure.
Figure 3B:
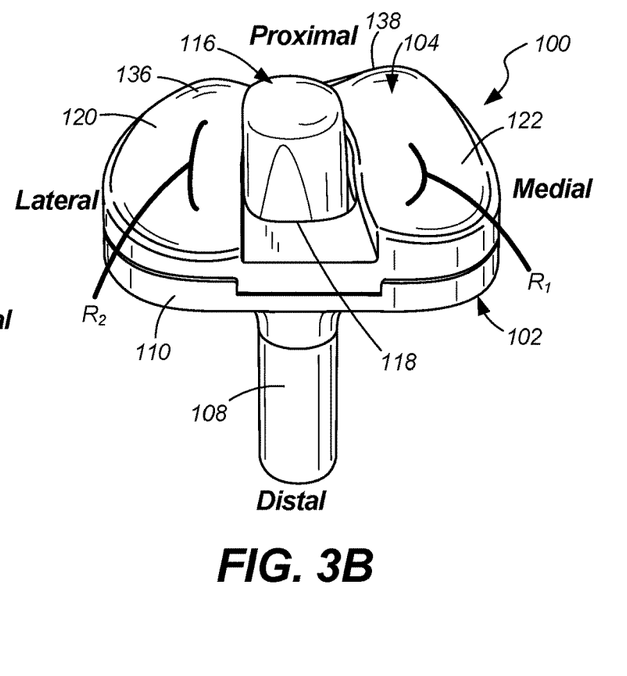
FIG. 3B illustrates an isometric view of an implant assembly in a first condition from a proximal-posterior perspective, in accordance with at least one example of the present disclosure.
Figure 4A:
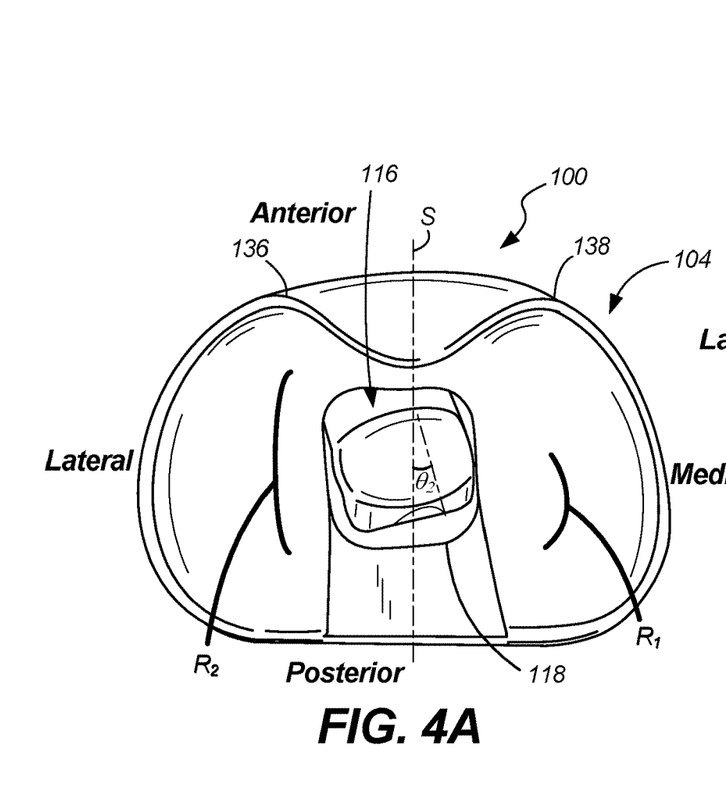
FIG. 4A illustrates a plan view of an implant assembly in a second condition, in accordance with at least one example of the present disclosure.
Figure 4B:
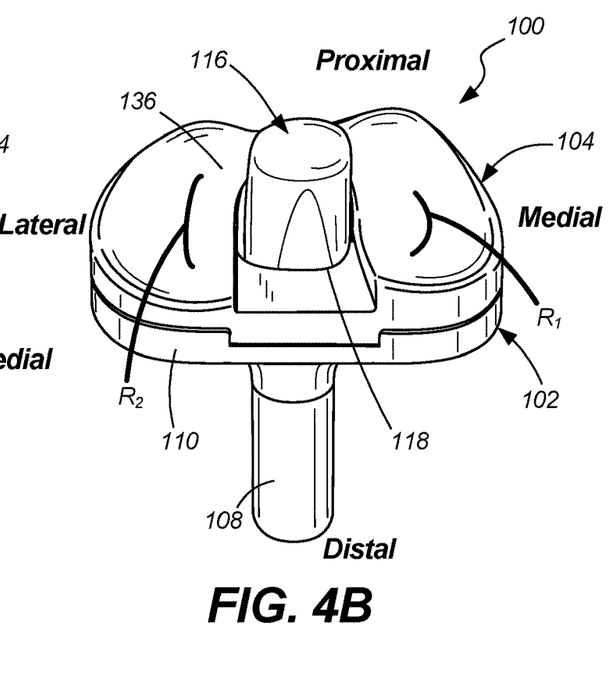
FIG. 4B illustrates an isometric view of an implant assembly in a second condition from a proximal-posterior perspective, in accordance with at least one example of the present disclosure.

FIG. 3A illustrates a plan view of implant assembly 100 in a first condition, in accordance with at least one example of the present disclosure. FIG. 3B illustrates an isometric view of implant assembly 100 in a first condition from a proximal-posterior perspective, in accordance with at least one example of the present disclosure. FIG. 4A illustrates a plan view of implant assembly 100 in a second condition, in accordance with at least one example of the present disclosure. FIG. 4B illustrates an isometric view of implant assembly 100 in a second condition from a proximal-posterior perspective, in accordance with at least one example of the present disclosure. FIGS. 3A, 3B, 4A, and 4B are discussed below concurrently.

Implant assembly 100 can include tibial component 102, tibial bearing 104, and post 116. Tibial component 102 can include tibial stem 108 and tibial baseplate 110. Tibial bearing 104 can include aperture 118, lateral bearing portion 120, and medial bearing portion 122. Lateral bearing portion 120 can include lip 136 and radius R2. Medial bearing portion 122 can include lip 138 radius R1. Also shown in FIGS. 3A and 4A are sagittal plane S, angles θ1 and θ2 and orientation indicators Anterior, Posterior, Medial, and Lateral. Also shown in FIGS. 3B and 4B are orientation indicators Anterior, Posterior, Proximal, and Distal.

Implant assembly 100 of FIGS. 3A-4B can be consistent with implant assembly 100 of FIGS. 1A-2B; however, FIGS. 3A-4B illustrate additional details of implant assembly. For example, FIG. 3A illustrates how post 116 can rotate clockwise to angle θ1 relative to the sagittal plane S, which can be an angle of 1, 2, 3, 4, 5, 6, 7, 8, 9, 10, 11, 12, 14, 16, 18, 20, 25 degrees, and the like. Rotation of post 116 to angle θ1 can be promoted during extension by asymmetrically curved lateral portion 120 and medial portion 122 of tibial bearing 104. For example, lateral portion 120 can have radius R1 which can be a radius of curvature of lateral portion 120 that extends into and along the transverse plane of tibial bearing 104. Medial portion 122 can have radius R2 which can be a radius of curvature of medial portion 122 that extends into and along the transverse plane of tibial bearing 104, where radius R2 is a greater radius than R1. That is, radius R2 creates a larger dish in medial portion 122 than a dish created by R1 of lateral portion 120. This asymmetry can promote rotation of post 116 substantially about medial portion 122 to allow rollback of the lateral condyle, as discussed above. Similarly, during flexion, post 116 can rotate counterclockwise to angle θ2 relative to the sagittal plane S, which can be an angle of 1, 2, 3, 4, 5, 6, 7, 8, 9, 10, 11, 12, 14, 16, 18, 20, 25 degrees, and the like.

FIGS. 3A, 3B, 4A and 4B also show lip 136 of lateral portion 120 of tibial bearing 104 and lip 138 of medial portion 122 of tibial bearing 104. Each of lip 136 and 138 can extend substantially proximally from tibial bearing 104. Lips 136 and 138 can be used to help limit translation and movement of femoral condyles. For example, lips 136 and 138 can limit translation of the femoral condyles anteriorly relative to tibial bearing 104.

In some examples, as shown in FIGS. 3B and 4B, medial lip 138 can extend further proximally than lateral lip 136. Because of this, in operation, medial lip 138 can limit translation of a medial condyle more than lateral lip 136 limits translation of a lateral condyle. The asymmetric lip lengths can thereby promote more movement of the lateral condyle than the medial condyle and, together with the varying radii R1 and R2 and rotation of post 116, can help promote a medially biased pivot of the condyles and therefore asymmetric femoral rollback.

The maximum rotation of post 116 in flexion and extension can be controlled by the walls of post and of aperture 118 as described above with respect to FIGS. 2A and 2B. In some examples, maximum rotation of post 116 relative to tibial bearing 104 can be the same for angle θ1 (flexion) and angle θ2 (extension). In other examples, the faces of post 116 and aperture 118 can be configured to allow different maximum flexion rotation (angle θ1) than extension rotation (angle θ2).

Figure 5A:
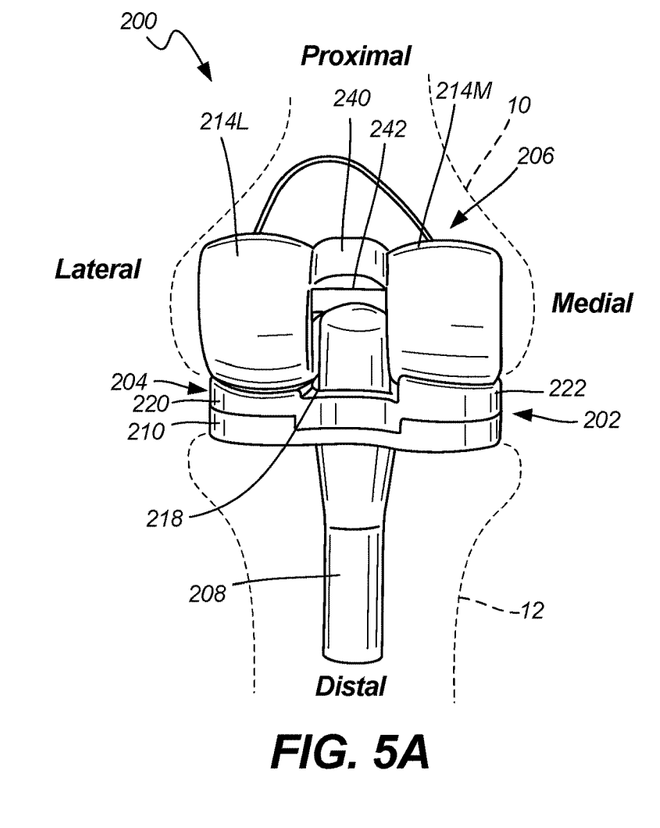
FIG. 5A illustrates an elevation view of an implant assembly in a first condition from a posterior perspective, in accordance with at least one example of the present disclosure.
Figure 5B:
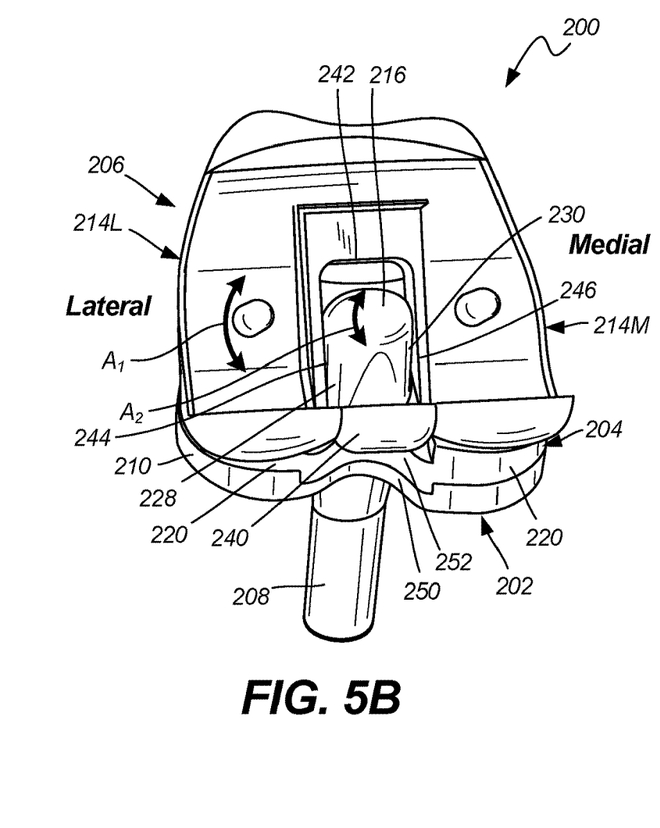
FIG. 5B illustrates an isometric view of an implant assembly in a second condition from a proximal posterior perspective, in accordance with at least one example of the present disclosure.

FIG. 5A illustrates an elevation view of implant assembly 200 in a first condition from a posterior perspective, in accordance with at least one example of the present disclosure. FIG. 5B illustrates an isometric view of implant assembly 200 in a second condition from a proximal posterior perspective, in accordance with at least one example of the present disclosure. FIGS. 5A and 5B are discussed below concurrently.

Implant assembly 200 can include tibial component 202, tibial bearing 204, femoral component 206, and post 216. Tibial component 202 can include tibial stem 208 and tibial baseplate 210. Tibial bearing 204 can include aperture 218 (only shown in FIG. 5A), lateral bearing portion 220, and medial bearing portion 222. Femoral component 206 can include lateral condyle 214L, medial condyle 214M, cam 240, and post slot 242, which can include faces 244 and 246. Post 216 can include faces 228 and 230. Tibial component 202 can also include retaining notch 250 and tibial bearing 204 can also include retaining notch 252. Also shown in FIG. 5A are femur 10, tibia 12, and orientation indicators Medial, Lateral, Proximal, and Distal. Also shown in FIG. 5B are arc A1, arc A2, pivot P, and orientation indicators Lateral and Medial.

Implant assembly 200 can be similar to implant assembly 100 discussed above, except that implant assembly 200 includes retaining notch 250 of tibial component 202 and retaining notch 252 of tibial bearing 204. In some examples retaining notches 250 and 252 can allow for a ligament, such as posterior cruciate ligament (PCL) to be connected to femur 10 and tibia 12 without interference with implant assembly 100. This allows implant assembly 200 to be a cruciate retaining TKA prosthesis.

FIG. 5A shows that tibial component 202 can be secured to tibia 12 and that femoral component 206 can be secured to femur 10. Also, FIGS. 5A and 5B show how femoral component 206 can interact with tibial bearing 204 and post 216. For example, FIGS. 5A and 5B show that lateral condyle 514L can interface with lateral portion 220 of bearing 204 and that medial condyle 514M can interface with medial portion 222 of bearing 204. FIGS. 5A and 5B further show how post 216 can extend through post slot 242 of femoral component 206 and into intercondylar fossa, where post slot 242 can be a slot defined at least partially by cam 240 and condyles 214 and can be alignable with an intercondylar fossa of femur 10.

FIG. 5B also shows how post 216 can engage post slot 242 (and the intercondylar fossa) to rotate with femoral component 206 (in a counterclockwise direction in FIG. 5B). For example, lateral face 228 of post 216 can engage lateral wall 244 of post slot 242 to rotate post 216 together with femoral component 206. Similarly, medial face 230 of post 216 can engage medial wall 246 of post slot 242 to rotate post 216 together with femoral component 206. This engagement allows for rotation of lateral condyle 214L along arc A1 while post rotates along arc A2 while medial condyle 214M substantially pivots about pivot P.

In some embodiments, cam 240 can engage a posterior face of post 216, which can be substantially flat (such as posterior face 134 of FIG. 2B), which can provide an articular surface for cam 240 and which can limit movement of femoral component 206 relative to tibial component 202 and tibial bearing 204, such as during flexion.

Figure 6:
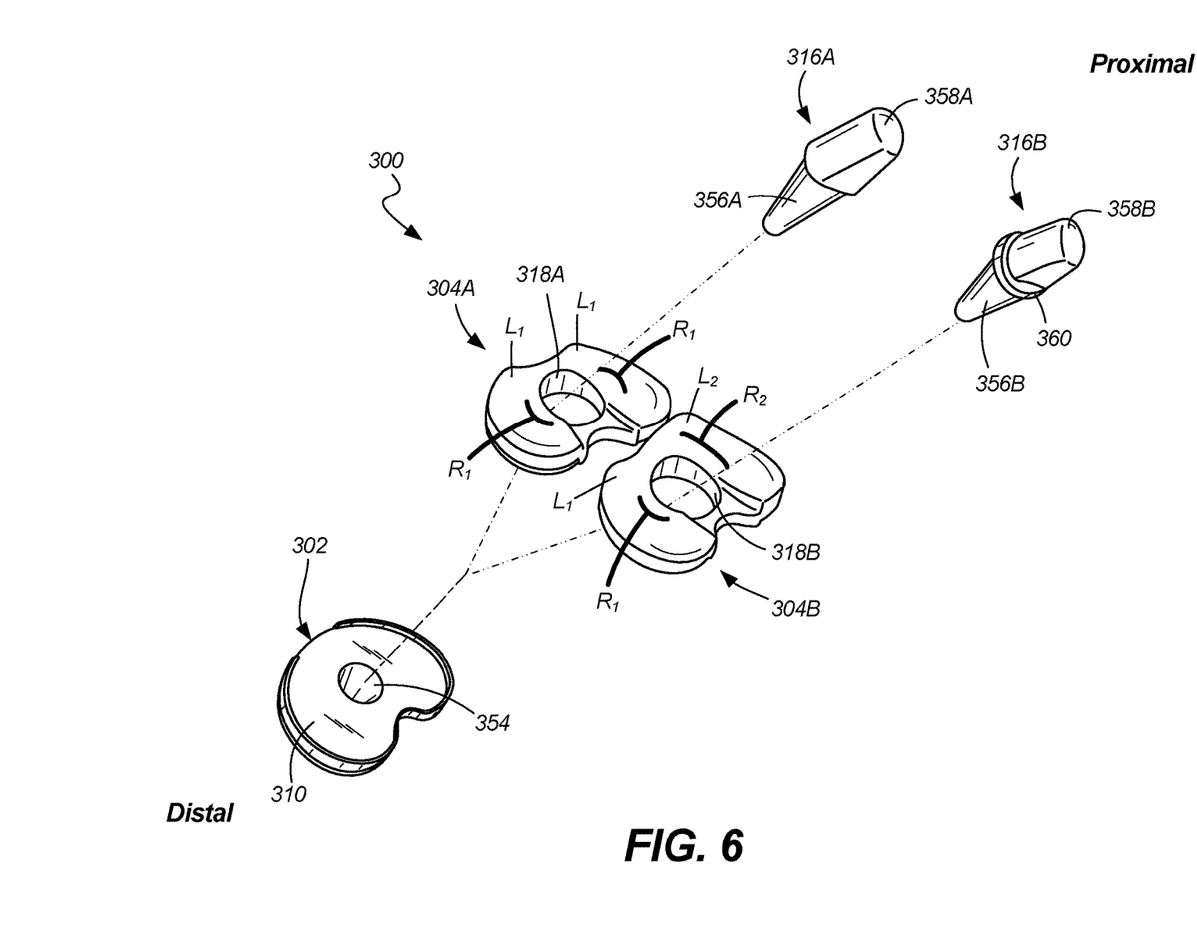
FIG. 6 illustrates an exploded view of an implant assembly kit, in accordance with at least one example of the present disclosure.

FIG. 6 illustrates an exploded view of implant assembly 300, in accordance with at least one example of the present disclosure. Implant assembly kit 300 can include tibial component 302, tibial bearing 304A, tibial bearing 304B, post 316A, and post 316B. Tibial component 302 can include baseplate 310 and stem cavity 354. Tibial bearing 304A can include lips L1 and bearing radii R1. Tibial bearing 304B can include lips L1 and L2 and bearing radii R1 and R2. Post 316A can include distal tapered portion 356A and proximal projection 358A. Post 316B can include distal projection 356B, proximal projection 358B, and collar 360.

Implant assembly 300 can be similar to implant assemblies 100 and 200 discussed above; however, FIG. 6 shows how implant assembly 300 can be a kit that can include multiple components that can change the way that implant assembly 300 operates following installation. For example, tibial bearings 304A and 304B can differ in that tibial bearing 304A can include lips L1 which can be lips extending a similar distance proximally from tibial bearing 304A. Further, tibial bearing 304A can include radii R1 which can be radii of curvature of medial and lateral portions that are similar or the same. By having lips L1 and radii R1, tibial bearing 304A can promote symmetric movement (rotation and translation) of the femoral component relative to tibial bearing 304. Meanwhile, tibial bearing 304B can include lips L1 and L2 which can extend different proximal distances from tibial bearing 304B. Further, tibial bearing 304B can include differing radii R1 and R2 (similar to tibial bearings 104 and 204). Together, lips L1 and L2 and radii R1 and R2 can promote asymmetric rollback of femoral condyles (as discussed above with respect to implant assemblies 100 and 200). By including bearings 304A and 304B, a physician can select a bearing based on the type of rollback (asymmetric or symmetric) that is determined to be a better choice for the patient.

Similarly, implant assembly 300 can include different posts 316A and 316B. Each of posts 316A and 316B can have similar distal projections (356A and 356B) to allow each of posts 316A and 316B to rotate within stem cavity 354. However, posts 316A and 316B can be different in that proximal projection 358A of post 316A can be wider (medially-to-laterally) than proximal projection 358B of post 316B. This can allow post 316A to further limit movement of the femoral component relative to tibial bearing 304 and tibial component 302. Though proximal projection 358B is narrower to allow for more movement of the femoral component relative to tibial component 302, post 316B can include collar 360 to engage aperture 318 to limit movement (translation) of post 316B relative to tibial bearing 304 and tibial component 302 while still allowing for rotation of post 316B within stem cavity 354. By including posts 316A and 316B, a physician can select a post based on a desired amount of movement of a femoral component relative to tibial component 302 and tibial bearing 304.

Figure 7:
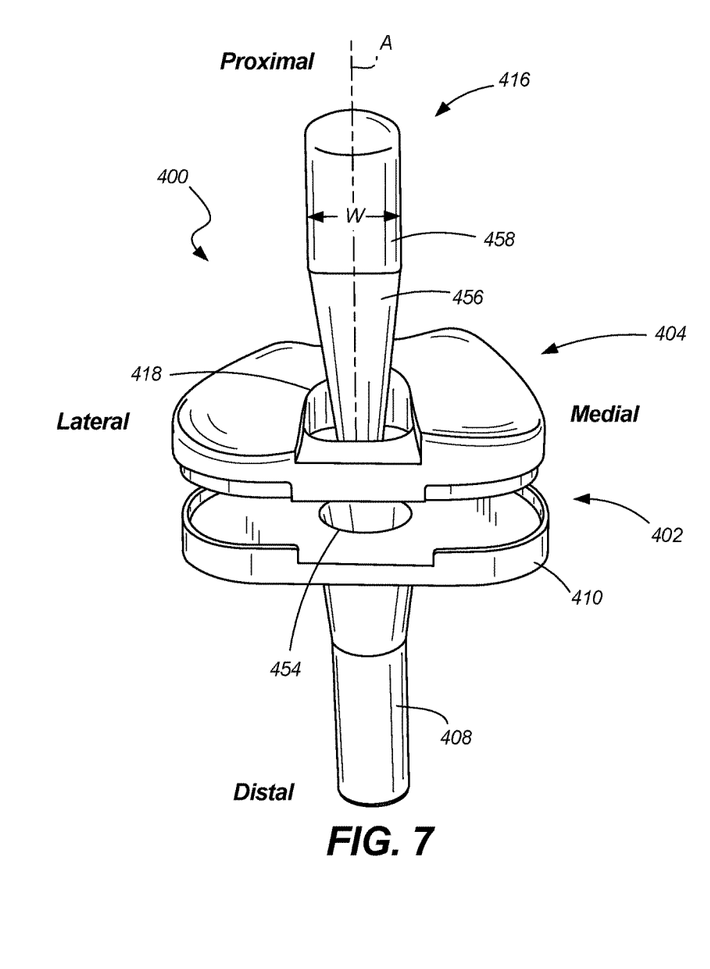
FIG. 7 illustrates a partially exploded view of an implant assembly from a proximal-posterior perspective, in accordance with at least one example of the present disclosure.

FIG. 7 illustrates a partially exploded view of implant assembly 400 from a proximal-posterior perspective, in accordance with at least one example of the present disclosure. Implant assembly 400 can include tibial component 402, tibial bearing 404, and post 416. Tibial component 402 can include stem 408 (which can include stem cavity 454) and tibial tray 410. Tibial bearing 404 can include aperture 418. Post 416 can include distal tapered portion 456 and proximal projection 458. Also shown in FIG. 7 is width W, axis X, and orientation indicators, Medial, Lateral, Proximal, and Distal.

Implant 400 can be similar to implants 100, 200, and 300 discussed above, in some examples. FIG. 7 shows how post 416 can be inserted through aperture 418 of tibial bearing 404 and into stem cavity 454 of tibial component 402. Because post 416 can be passed through aperture 418 of tibial bearing 404, post 416 can be inserted into stem cavity 454 either before or after tibial bearing is placed on tibial tray 410 of tibial component 404. Further, post 416 can be removed from stem cavity 454 while tibial bearing 404 is installed on tibial tray 410. This can reduce the number of steps required when a physician is choosing a post during a total or partial knee arthroplasty. Similarly, this can reduce the number of steps required to replace a post during a revision procedure.

FIG. 7 also shows that post 416 can have a width w (in a medial-lateral direction) that can be varied, in some examples. Width w of post 416 can be selected to provide a desired amount of freedom of movement of a femoral component relative to tibial component 402 and tibial bearing 404 (such as femoral component 106 of FIG. 1) when the femoral component and intercondylar fossa engages and interacts with post 416. For example, if less relative movement (such as medial-lateral movement) of the femoral component is desired, a large width w of post 416 can be selected and if more relative movement is allowable (such as in a cruciate retaining TKA), post 416 having a smaller width w may be selected.

Width w of post 416 can be selected can also be selected to limit movement of post 416 relative to tibial bearing 404. For example, width w can be selected to limit rotation of post 416 transverse to axis X while still allowing rotation of post 416 about axis X. In other examples, other dimensions of the post (such as a posterior-anterior length) can also be varied as desired to limit movement of post 416.

Figure 8A:
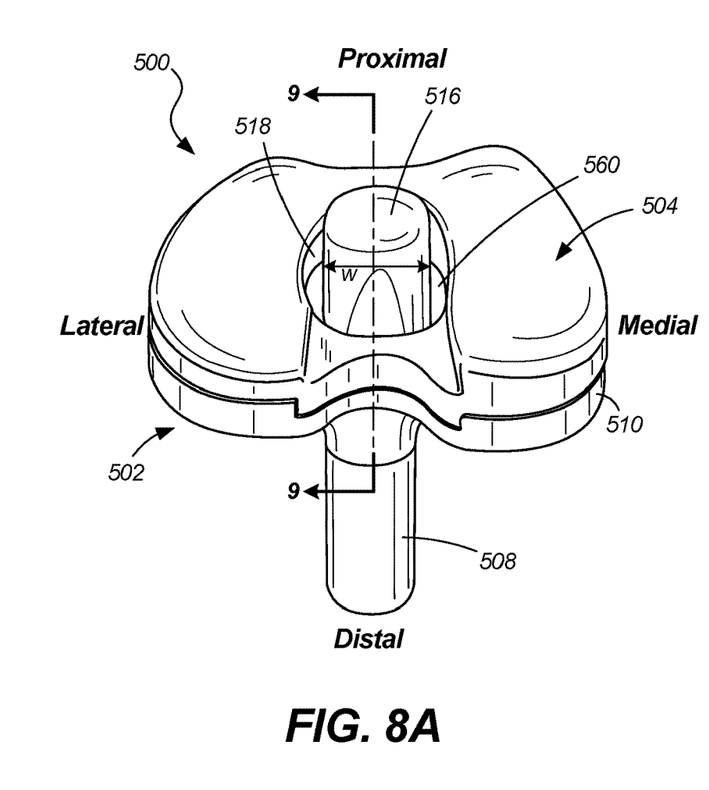
FIG. 8A illustrates an elevation view of an implant assembly in a first condition from a proximal-posterior perspective, in accordance with at least one example of the present disclosure.
Figure 8B:
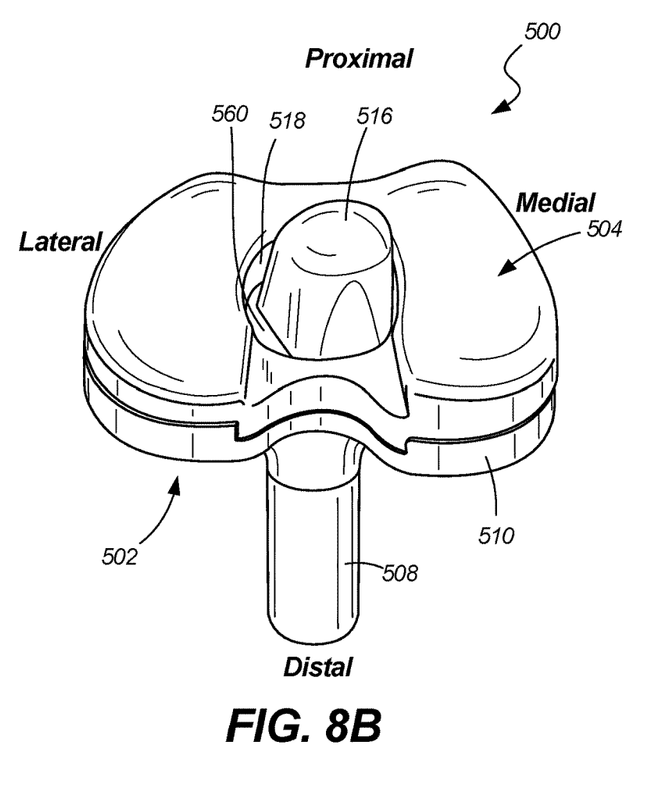
FIG. 8B illustrates an isometric view of an implant assembly in a second condition from a proximal-posterior perspective, in accordance with at least one example of the present disclosure.

FIG. 8A illustrates an elevation view of implant assembly 500 in a first condition from a proximal-posterior perspective, in accordance with at least one example of the present disclosure. FIG. 8B illustrates an isometric view of implant assembly 500 in a second condition from a proximal-posterior perspective, in accordance with at least one example of the present disclosure. FIGS. 8A and 8B are discussed below concurrently.

Implant assembly 500 can include tibial component 502, tibial bearing 504, and post 516. Tibial component 502 can include stem 508 (which can include stem cavity 554) and tibial tray 510. Tibial bearing 504 can include aperture 518. Post 516 can include distal tapered portion 556, proximal projection 558, and collar 560. Also shown in FIG. 8 is width w, and orientation indicators, Medial, Lateral, Proximal, and Distal.

Implant assembly 500 of FIGS. 8A and 8B can be similar to implant assemblies 100, 200, 300, and 400 discussed above with respect to FIGS. 1-7; however, FIGS. 8A and 8B illustrate post 516 inserted into stem cavity 554, where FIG. 8A shows post 516 in a neutral position and FIG. 8B shows post 516 rotated counter-clockwise from the neutral position. FIGS. 8A and 8B also show post 516 having a width w that is substantially smaller than a width of aperture 518, which can allow more medial-lateral movement of a femoral component engaged with post 516 relative to tibial component 502 and tibial bearing 504.

FIGS. 8A and 8B also show collar 560 disposed in aperture 518, which can allow for post 516 to have a smaller width to enable femoral medial-lateral movement (discussed above). However, by engaging bearing 504, collar 560 can limit movement of post 516 transverse to an axis of the post (medial-lateral and/or anterior-posterior) while still allowing for axial rotation of post 516 within stem 508.

Figure 9:
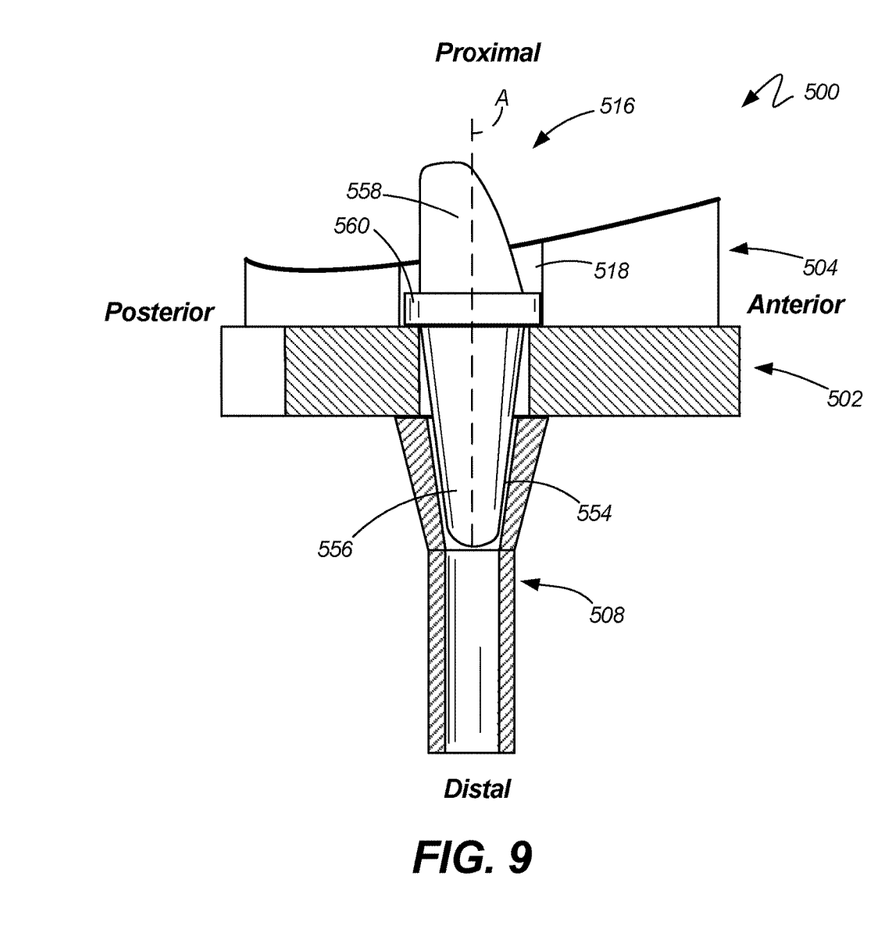
FIG. 9 illustrates a cross-sectional view of an implant assembly from a medial perspective, in accordance with at least one example of the present disclosure.

FIG. 9 illustrates a cross-sectional view of implant assembly 500 across indicators 9-9 of FIG. 8A, in accordance with at least one example of the present disclosure. Implant assembly 500 can include tibial component 502, tibial bearing 504, and post 516. Tibial component 502 can include stem 508 (which can include stem cavity 554) and tibial tray 510. Tibial bearing 504 can include aperture 518. Post 516 can include distal tapered portion 556, proximal projection 558, and collar 560. Also shown in FIG. 8 is axis X, and orientation indicators, Medial, Lateral, Anterior, and Posterior.

Implant assembly 500 of FIG. 9 can be the same as implant assembly 500 discussed above with respect to FIGS. 8A and 8B; however, FIG. 9 illustrate post 516 inserted into stem cavity 554.

Distal projection 556 can be sized and shaped to be inserted through aperture 518 proximally-to-distally and can be sized and shaped to be disposed in stem cavity 554. In some examples, distal projection 556 substantially conical in geometric shape (or tapered toward a distal side) and stem cavity can be a complementary shape (conical/tapered bore) to allow smooth rotation of distal projection 556 when engaging stem cavity 554. The taper-to-taper engagement can also reduce movement of post 516 transverse to axis X (medial-lateral and/or anterior-posterior) relative to stem cavity 554 and therefore relative to tibial component 502 and tibial bearing 504.

FIG. 9 also shows how collar 560 can limit a distance that distal projection 556 is inserted into stem cavity 554, which can help to control a proximal distance that post 516 extends from tibial component 502. FIG. 9 further shows how collar 560 can be disposed within aperture 518 such that collar 560 is free to rotate within aperture 518 without interference caused by contact of collar 560 with aperture 518. However, collar 560 can be placed close enough to aperture 518 to cause contact between collar 560 and aperture 518 to limit movement of post 516 transverse to axis X (medial-lateral and/or anterior-posterior) relative to stem cavity 554 and therefore relative to tibial component 502 and tibial bearing 504. Post 516 is therefore redundantly limited from moving transversely to axis X.

Figure 10:
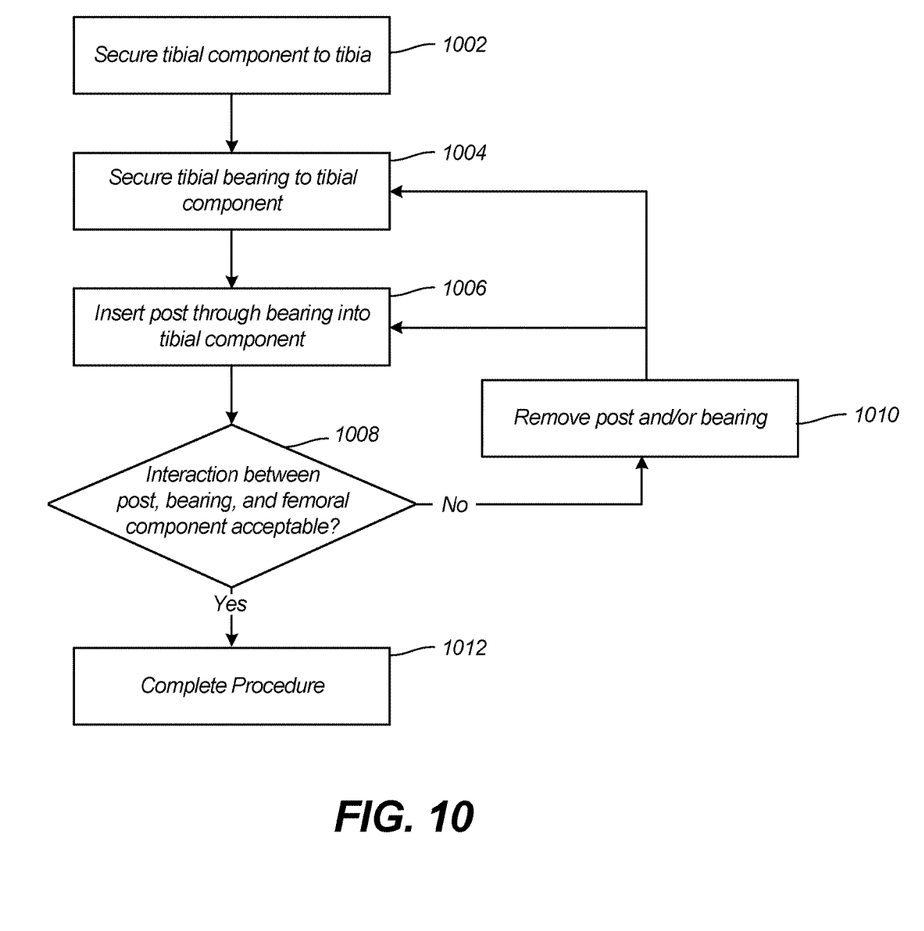
FIG. 10 illustrates a flow schematic of a method, in accordance with at least one example of the present disclosure.

FIG. 10 illustrates a flow schematic of method 1000, in accordance with at least one example of the present disclosure. The steps or operations of method 1000 are illustrated in a particular order for convenience and clarity; many of the discussed operations can be performed in a different sequence or in parallel, and some operations may be excluded, without materially impacting other operations. The method 1000, as discussed, includes operations performed by multiple different actors, devices, and/or systems. It is understood that subsets of the operations discussed in the method 1000 attributable to a single actor, device, or system could be considered a separate, standalone, process or method.

In some examples, method 1000 can be a method of installing a implant assembly during a knee arthroplasty on a tibia and/or a femur. Prior to step 1002, the tibia can be resected using cut blocks and hand or power tools and an intramedullary canal of the tibia can be reamed. Similarly, the femoral condyles can be resected and the intramedullary canal of the femur can be reamed. In one example, method 1000 can begin at step 1002, where a tibial component can be secured to a resected proximal portion of a tibia. For example, tibial component 202 can be secured to tibia 12 (where stem 208 can be inserted into the intramedullary canal of tibia 12). At step 1004 a tibial bearing can be secured to the tibial component. For example, tibial bearing 204 can be secured to tibial component 202.

Then, at step 206, a post can be inserted through the tibial bearing into the stem of the tibial component. For example, post 216 can be inserted through aperture 218 of tibial bearing 204 into a post cavity of stem 208 of tibial component 202. Between or before steps 1006 and 1008 a femoral component can be secured to a femur. For example, femoral component 206 can be secured to femur 10. In other examples, the femoral component may not be secured to the femur. In either example, the femoral component can be engaged with the post and tibial bearing and operation of the femoral component, post, and tibial component can be observed at step 1008 and it can be determined whether the interaction is acceptable. For example, interaction between femoral component 206, post 216, and tibial bearing 204 can be examined by articulating the tibia relative to the femur or by articulating the femoral component relative to the tibial component.

If it is determined that the interaction between any of the femoral component, post, and tibial component is undesirable, the post and/or tibial component can be removed at step 1010 and steps 1004 and/or 1006 can be repeated along with step 1008. When it is determined that the interaction between the femora component, post, and tibial component is acceptable, the procedure can be completed at step 1012, which can include further securing any of the tibial component, femoral component, tibial bearing, and post, and can further include closure of openings, etc.

Examples

To further illustrate the apparatuses and systems disclosed herein, the following non-limiting examples are provided:

Example 1 is a knee joint prosthesis for a human tibia and femur, the knee joint prosthesis comprising: a tibial component comprising: a tibial baseplate comprising a proximal surface including a sagittal axis, and an opposing distal surface; and a tibial stem extending from the distal surface of the tibial baseplate and including a cavity therein; a tibial bearing disposable on the proximal surface of the tibial baseplate, the tibial bearing comprising: a first bearing portion positionable on a first side of the sagittal axis and having a first shape; a second bearing portion positionable on a second side of the sagittal axis and having a second shape different than the first shape; and an aperture alignable with the cavity of the tibial stem; and a post extendable through the aperture of the tibial bearing and disposable in the cavity of the tibial component, the post rotatable relative to the tibial baseplate and the tibial bearing, the post together with the first bearing portion and the second bearing portion configured to promote the femur to substantially pivot about the first bearing portion.

In Example 2, the subject matter of Example 1 optionally includes wherein the post and the tibial bearing are shaped to promote asymmetric anteroposterior rollback of a lateral femoral condyle of the femur at a faster rate than rollback of a medial femoral condyle.

In Example 3, the subject matter of any one or more of Examples 1-2 optionally include wherein the first bearing portion is a medial portion of the bearing.

In Example 4, the subject matter of any one or more of Examples 1-3 optionally include wherein the first shape of the first portion of the tibial bearing comprises a first radius of curvature that is smaller than a second radius of curvature of the second shape of the second portion of the tibial bearing.

In Example 5, the subject matter of any one or more of Examples 1-4 optionally include wherein rotation of the post relative to the tibial bearing is limited by contact between the post and the bearing.

In Example 6, the subject matter of any one or more of Examples 1-5 optionally include the post further comprising: a medial side that is substantially flat; a lateral side opposing the medial side, the lateral side being substantially flat to allow rollback; an anterior face connecting the medial side and the lateral side; and a posterior face opposing the anterior face and connecting the medial side and the lateral side.

In Example 7, the subject matter of Example 6 optionally includes wherein rotation of the post relative to the tibial bearing is limited by contact between the bearing and edges of the medial side of the post and edges of the lateral side of the post.

In Example 8, the subject matter of any one or more of Examples 6-7 optionally include wherein movement of the post out of the cavity is limited by contact between the bearing and the anterior face of the post.

In Example 9, the subject matter of any one or more of Examples 6-8 optionally include wherein the anterior face is tapered as the post extends superiorly.

Example 10 is a knee joint prosthesis for a human tibia and femur, the knee joint prosthesis comprising: a tibial component comprising: a tibial baseplate comprising a proximal surface including a sagittal axis, and an opposing distal surface; and a tibial stem extending from the distal surface of the tibial baseplate and including a cavity therein; a tibial bearing disposable on the proximal surface of the tibial baseplate, the tibial bearing comprising: a first bearing portion positionable on a first side of the sagittal axis and having a first shape; a second bearing portion positionable on a second side of the sagittal axis and having a second shape different than the first shape; and an aperture alignable with the cavity of the tibial stem; and a post extendable through the aperture of the tibial bearing and disposable in the cavity of the tibial component, the post rotatable relative to the tibial baseplate and the tibial bearing, the post together with the first bearing portion and the second bearing portion configured to promote rotation of the femur with a medial bias.

In Example 11, the subject matter of Example 10 optionally includes wherein the tibial baseplate further comprises a baseplate PCL notch, and wherein the tibial bearing further comprises a bearing PCL notch alginable with the baseplate PCL notch when the bearing is disposed on the tibial baseplate, the baseplate PCL notch and the bearing PCL notch configured to receive a PCL therein.

In Example 12, the subject matter of any one or more of Examples 10-11 optionally include wherein the post is free to rotate entirely within the cavity and the aperture.

In Example 13, the subject matter of any one or more of Examples 10-12 optionally include wherein the post is insertable through the aperture of the tibial bearing and into the cavity of the tibial baseplate after the bearing is disposed on the tibial plate.

In Example 14, the subject matter of any one or more of Examples 10-13 optionally include wherein the post and a the first shape of the first bearing portion and the second shape of the second bearing portion of the tibial bearing are configured to limit translation of the femur relative to the tibia along a transverse plane.

In Example 15, the subject matter of any one or more of Examples 10-14 optionally include the post further comprising: a collar extending radially from the post and engageable with the tibial baseplate around the cavity and engageable with the bearing aperture to limit movement of the femur along a coronal plane of the femur.

In Example 16, the subject matter of any one or more of Examples 10-15 optionally include wherein the post and the tibial bearing are shaped to promote asymmetric anteroposterior rollback of a lateral femoral condyle of the femur at a faster rate than rollback of a medial femoral condyle.

In Example 17, the subject matter of any one or more of Examples 10-16 optionally include wherein the first shape of the first portion of the tibial bearing comprises a first radius of curvature that is smaller than a second radius of curvature of the second shape of the second portion of the tibial bearing.

Example 18 is a knee joint prosthesis assembly for a human tibia and femur, the knee joint prosthesis comprising: a tibial component comprising: a tibial baseplate comprising a proximal surface including a sagittal axis, and an opposing distal surface; and a tibial stem extending from the distal surface of the tibial baseplate and including a cavity therein; a tibial bearing disposable on the proximal surface of the tibial baseplate, the tibial bearing comprising: a first bearing portion positionable on a first side of the sagittal axis and having a first shape; a second bearing portion positionable on a second side of the sagittal axis and having a second shape different than the first shape; and an aperture alignable with the cavity of the tibial stem; and a post extendable through the aperture of the tibial bearing and disposable in the cavity of the tibial component, the post rotatable relative to the tibial baseplate and the tibial bearing, the post together with the first bearing portion and the second bearing portion configured to promote the femur to promote rotation of the femur with a medial bias; and a femoral component including a lateral condyle, a medial condyle, and an intercondylar fossa disposed between the lateral and medial condyles, the femoral component articulable on the tibial bearing.

In Example 19, the subject matter of Example 18 optionally includes wherein the post is selectable from a plurality of posts to provide a desired amount of movement of the femoral component relative to the tibial bearing along a coronal plane of the femur.

In Example 20, the subject matter of any one or more of Examples 18-19 optionally include wherein the tibial bearing is selectable from a plurality of tibial bearings to provide a desired amount of medial bias of rotation of the medial condyle about the tibial bearing.

In Example 21, the subject matter of any one or more of Examples 18-20 optionally include wherein the tibial bearing is selectable from a plurality of tibial bearings to provide an ability to insert the post without removing the tibial bearing.

In Example 22, the apparatuses or method of any one or any combination of Examples 1-22 can optionally be configured such that all elements or options recited are available to use or select from.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. A knee joint prosthesis for a human tibia and femur, the knee joint prosthesis comprising:
a tibial component comprising:
a tibial baseplate comprising a proximal surface including a sagittal axis, and an opposing distal surface; and
a tibial stem extending from the distal surface of the tibial baseplate and including a cavity therein;
a tibial bearing disposable on the proximal surface of the tibial baseplate, the tibial bearing comprising:
a first bearing portion positionable on a first side of the sagittal axis and having a first shape;
a second bearing portion positionable on a second side of the sagittal axis and having a second shape different than the first shape; and
an aperture alignable with the cavity of the tibial stem;
a post extendable through the aperture of the tibial bearing and disposable in the cavity of the tibial component, the post rotatable relative to the tibial baseplate and the tibial bearing, the post together with the first bearing portion and the second bearing portion configured to promote the femur to substantially pivot about the first bearing portion; and
a collar extending radially from the post and engageable with the tibial baseplate around the cavity and engageable with the bearing aperture to limit movement of the femur along a coronal plane of the femur.

2. The knee joint prosthesis of claim 1, wherein the post and the tibial bearing are shaped to promote asymmetric anteroposterior rollback of a lateral femoral condyle of the femur at a faster rate than rollback of a medial femoral condyle.

3. The knee joint prosthesis of claim 1, wherein the first bearing portion is a medial portion of the bearing.

4. The knee joint prosthesis of claim 1, wherein the first shape of the first portion of the tibial bearing comprises a first radius of curvature that is smaller than a second radius of curvature of the second shape of the second portion of the tibial bearing.

5. The knee joint prosthesis of claim 1, wherein rotation of the post relative to the tibial bearing is limited by contact between the post and the bearing.

6. The knee joint prosthesis of claim 1, the post further comprising:
a medial side that is substantially flat;
a lateral side opposing the medial side, the lateral side being substantially flat to allow rollback;
an anterior face connecting the medial side and the lateral side; and
a posterior face opposing the anterior face and connecting the medial side and the lateral side.

7. The knee joint prosthesis of claim 6, wherein rotation of the post relative to the tibial bearing is limited by contact between the bearing and edges of the medial side of the post and edges of the lateral side of the post.

8. The knee joint prosthesis of claim 6, wherein movement of the post out of the cavity is limited by contact between the bearing and the anterior face of the post.

9. The knee joint prosthesis of claim 6, wherein the anterior face is tapered as the post extends superiorly.

10. A knee joint prosthesis for a human tibia and femur, the knee joint prosthesis comprising:
a tibial component comprising:
a tibial baseplate comprising a proximal surface including a sagittal axis, and an opposing distal surface; and
a tibial stem extending from the distal surface of the tibial baseplate and including a cavity therein;
a tibial bearing disposable on the proximal surface of the tibial baseplate, the tibial bearing comprising:
a first bearing portion positionable on a first side of the sagittal axis and having a first shape;
a second bearing portion positionable on a second side of the sagittal axis and having a second shape different than the first shape; and
an aperture alignable with the cavity of the tibial stem;
a post extendable through the aperture of the tibial bearing and disposable in the cavity of the tibial component, the post rotatable relative to the tibial baseplate and the tibial bearing, the post together with the first bearing portion and the second bearing portion configured to promote rotation of the femur with a medial bias; and
a collar extending radially from the post and engageable with the tibial baseplate around the cavity and engageable with the bearing aperture to limit movement of the femur along a coronal plane of the femur.

11. The knee joint prosthesis of claim 10, wherein the tibial baseplate further comprises a baseplate PCL notch, and wherein the tibial bearing further comprises a bearing PCL notch alignable with the baseplate PCL notch when the bearing is disposed on the tibial baseplate, the baseplate PCL notch and the bearing PCL notch configured to receive a PCL therein.

12. The knee joint prosthesis of claim 10, wherein the post is free to rotate entirely within the cavity and the aperture.

13. The knee joint prosthesis of claim 10, wherein the post is insertable through the aperture of the tibial bearing and into the cavity of the tibial baseplate after the bearing is disposed on the tibial plate.

14. The knee joint prosthesis of claim 10, wherein the post and the first shape of the first bearing portion and the second shape of the second bearing portion of the tibial bearing are configured to limit translation of the femur relative to the tibia along a transverse plane.

15. The knee joint prosthesis of claim 10, wherein the post and the tibial bearing are shaped to promote asymmetric anteroposterior rollback of a lateral femoral condyle of the femur at a faster rate than rollback of a medial femoral condyle.

16. The knee joint prosthesis of claim 10, wherein the first shape of the first portion of the tibial bearing comprises a first radius of curvature that is smaller than a second radius of curvature of the second shape of the second portion of the tibial bearing.

17. A knee joint prosthesis assembly for a human tibia and femur, the knee joint prosthesis comprising:
- a tibial component comprising:
  - a tibial baseplate comprising a proximal surface including a sagittal axis, and an opposing distal surface; and
  - a tibial stem extending from the distal surface of the tibial baseplate and including a cavity therein;
- a tibial bearing disposable on the proximal surface of the tibial baseplate, the tibial bearing comprising:
  - a first bearing portion positionable on a first side of the sagittal axis and having a first shape;
  - a second bearing portion positionable on a second side of the sagittal axis and having a second shape different than the first shape; and
  - an aperture alignable with the cavity of the tibial stem; and
- a post extendable through the aperture of the tibial bearing and disposable in the cavity of the tibial component, the post rotatable relative to the tibial baseplate and the tibial bearing;
- a femoral component including a lateral condyle, a medial condyle, and an intercondylar fossa disposed between the lateral and medial condyles, the femoral component articulable on the tibial bearing; and
- a collar extending radially from the post and engageable with the tibial baseplate around the cavity and engageable with the bearing aperture to limit movement of the femur along a coronal plane of the femur
- wherein the post together with the first bearing portion and the second bearing portion are configured to promote the femur to promote rollback of the lateral femoral condyle.

18. The knee joint prosthesis of claim 17, wherein the post is selectable from a plurality of posts to provide a desired amount of movement of the femoral component relative to the tibial bearing along a coronal plane of the femur.

19. The knee joint prosthesis of claim 17 wherein the tibial bearing is selectable from a plurality of tibial bearings to provide a desired amount of medial bias of rotation of the medial condyle about the tibial bearing.

20. The knee joint prosthesis of claim 17, wherein the tibial bearing is selectable from a plurality of tibial bearings to provide an ability to insert the post without removing the tibial bearing.

* * * * *